United States Patent [19]

Munari et al.

[11] Patent Number: 4,621,534
[45] Date of Patent: Nov. 11, 1986

[54] AUTOMATIC SAMPLE APPARATUS, VALVE AND SAMPLING METHOD

[75] Inventors: Fausto Munari, Milan; Bruno Tosi, Verano Brianza, both of Italy; Sorin Trestianu, Brussels, Belgium; Enzo Montagner, Pioltello, Italy

[73] Assignee: Carlo Erba Strumentazione S.p.A., Italy

[21] Appl. No.: 647,986

[22] Filed: Sep. 6, 1984

[30] Foreign Application Priority Data

Sep. 14, 1983 [IT] Italy .................. 22978/83[U]
Jun. 22, 1984 [IT] Italy .................. 21557 A/84
Jun. 29, 1984 [IT] Italy .................. 22433/84[U]

[51] Int. Cl.⁴ .............................................. G01N 1/00
[52] U.S. Cl. ................................................ 73/864.86
[58] Field of Search ............ 73/864.21, 864.22, 864.24, 73/864.81, 864.83, 864.84, 864.85, 864.86

[56] References Cited

U.S. PATENT DOCUMENTS

| | | | |
|---|---|---|---|
| 3,401,564 | 9/1968 | Hrdina ................. | 73/864.85 |
| 3,693,455 | 9/1972 | Harding et al. ........ | 73/864.86 |
| 3,748,911 | 7/1973 | Rousselet ............. | 73/864.25 |
| 3,841,160 | 10/1974 | Iwao ................... | 73/864.87 |
| 3,842,680 | 10/1974 | Vollick ................ | 73/864.22 |
| 3,911,749 | 10/1975 | Hendry ................ | 73/864.22 |
| 4,094,195 | 6/1978 | Friswell .............. | 73/864.21 |
| 4,454,749 | 6/1984 | Guillemin et al. ..... | 73/864.81 |
| 4,516,437 | 5/1985 | Pedroso et al. ....... | 73/864.22 |

Primary Examiner—Stewart J. Levy
Assistant Examiner—Robert R. Raevis
Attorney, Agent, or Firm—Lerner, David, Littenberg, Krumholz & Mentlik

[57] ABSTRACT

The present invention relates to an automatic sampling apparatus for sample injection into a gas chromatographic column. In order to allow automatic injection with a non-vaporizing direct on-column injector, the apparatus includes a switch valve, an on-column injector, and a pre-column each having a passage with a diameter greater than 0.5 mm for receiving the injection syringe. The present invention also relates to a device provided with a series of small arms for driving the needle during injection, a switch valve constructed and arranged in a manner to prevent any contamination of the injector by the sample during the injection step, as well as an injection method which can be used with the apparatus and switch valve.

23 Claims, 4 Drawing Figures

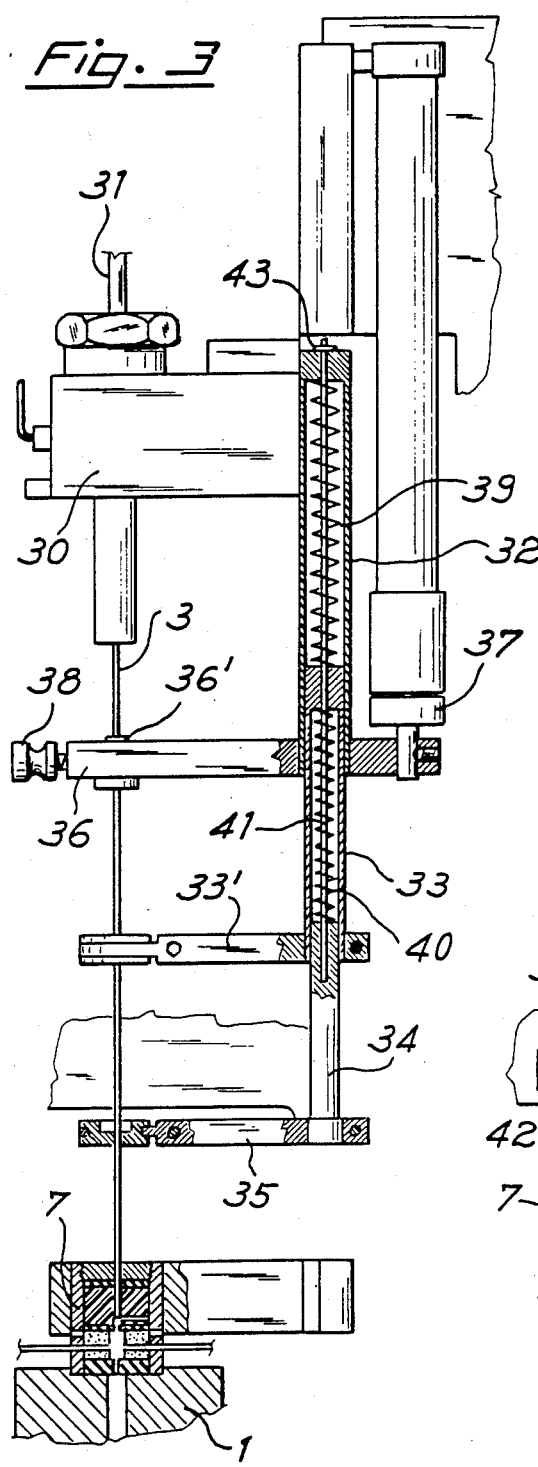
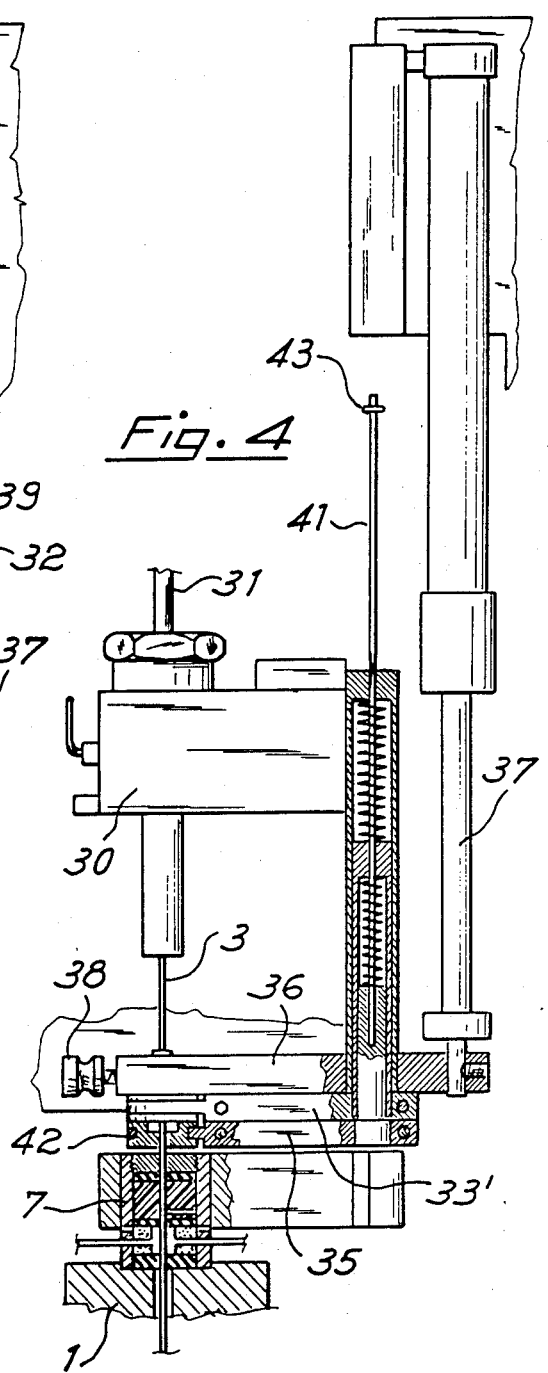

AUTOMATIC SAMPLE APPARATUS, VALVE AND SAMPLING METHOD

BACKGROUND OF THE INVENTION

The present invention relates to an automatic sampling apparatus for the injection of samples to be analyzed in a gas chromatographic column, and more particularly, to such an apparatus designed to be used in case of sample injections by means of non-vaporizing direct on-column injectors. The present invention further relates to a switch valve designed for such apparatus, as well as to a sampling method to be used with such apparatus and switch valve.

Among the equipment available to perform chemical analysis of liquid samples by gas chromatography, there are known automatic samplers which allow the feeding of a series of samples to be analyzed to an injector connected to the head of a gas chromatographic column. These automatic samplers are, for example, constructed in a manner which requires removal of the injection syringe from the sample vial and its insertion into the injector. However, these known automatic samplers possess many drawbacks. To this end, it is preferred to employ automatic samplers of the type where the injection syringe remains fixedly aligned with the injector.

These last mentioned automatic samplers generally include an automatic device which is capable of drawing the sample to be analyzed from a container, e.g., a vial, and of feeding it to an injection syringe mounted in alignment with the inlet part e.g., injection port, of an injector. Automatic means are provided which are capable of washing the whole sample feeding system in such a way that, at the end of the injection stage of each sample, the device is ready for feeding the syringe with a new sample, without the danger that the syringe is contaminated by traces of the previously injected sample. In addition, automatic means are provided which actuate the movement of the injection syringe needle into and out of the injector. Further, automatic means are provided for measuring the exact amount of sample to be introduced into the gas chromatographic column and automatic means are provided for introducing the sample into the gas chromatographic column. In order to drain the washing liquid and the excess sample coming out from the injection syringe, thus preventing them from penetrating the injector body and contaminating it, a switch valve is generally provided between the injection syringe and the injector.

The aforementioned known equipment, however, cannot be used with on-column type injectors. In particular, the first type does not provide perfect alignment between the syringe needle and the on-column injector, while the second type, as the first type, requires the use of sample injection syringes equipped with very thin needles which are capable of penetrating inside the gas chromatographic capillary column having an internal diameter of approximately 0.2-0.3 mm. The peculiarities of on-column injectors represents a considerable problem. That is, the aforementioned switch valve is generally constructed to include a rubber septa generally not pierceable by extremely thin needles, such as those used in on-column injectors. Moreover, the automatic means actuating the injection syringe needle movements into and out of the injector do not assure a sufficient precision of operation, as necessary for a safe introduction into the gas chromatographic column of the very thin and extremely flexible needle used with the on-column type injectors.

SUMMARY OF THE INVENTION

An object of the present invention is to provide an automatic sampling apparatus suitable for injection of samples to be analyzed by injectors of the non-vaporizing direct on-column type for gas chromatographic capillary columns.

Another object of the present invention is to provide, in a sampling apparatus of the above-described type, a device capable of driving the needle in its movements in a manner to ensure that distortions of the needle do not occur due to bending and compressive stresses acting on same, so that it is possible to reduce the diameter of the needle.

Still a further object of the present invention is to provide a switch valve for a sampling machine of the aforementioned type which, besides allowing drainage of the washing liquid and of any excess sample, without letting them penetrate the injector during these operations, also allows for the elimination of any traces of liquid in the vicinity of the needle end, as well as the external walls of the needle, in such a way that it is absolutely assured that during needle introduction into the injector, no traces of liquid sample are dragged by the needle inside the injector with the resulting injector pollution.

These objects of the present invention are achieved by means of an automatic sampling apparatus for the injection of samples to be analyzed in a gas chromatographic capillary column, which comprises an automatic device to introduce each sample into an injection syringe and to send washing fluid to the syringe itself, a switch valve for drainage of the sample and washing fluid, the valve being positioned coaxially to the syringe needle between the injector and the syringe itself, means to move the syringe and the needle thereof into and out of the injector, and means actuating the syringe, wherein the valve is mounted on an injector of the non-vaporizing direct on-column type, in which the diameter for the passage of the injection syringe needle is greater than or equal to 0.5 mm and in which the passage receives a pre-column connecting the injector to the gas chromatographic capillary column, the pre-column having a diameter greater than or equal to 0.5 mm.

In this way, it is now possible to have an injection syringe using needles having a suitable size to pass through the rubber septa of the switch valve without any distortion, while the aforementioned pre-column, having a diameter greater than or equal to 0.5 mm, allows safe and reliable introduction of the needle also using the automatic means actuating the injection syringe movement into and out of the injector.

In order to obtain the desired insulation of the injector and the chromatographic system from the external environment, the switch valve is pneumatically mounted on the injector body and is constantly fed, during the sample injection step, with carrier or inert gas.

Still according to the present invention, the needle is inserted into precision aligned holes of a series of small arms superimposed and spaced-apart between each other. Starting from the top of the needle, the first small arm is integral to the needle itself, is connected to the needle support by means of a vertical tube, and is connected to the mobile part of the device actuating the needle movement into and out of the injector. The underlying arms are each integral to sliding vertical tubes which are inserted in a telescopic manner with the tube of the first small arm. The underlying arms are each provided with a hole in which the needle is inserted in sliding relationship and are kept spaced-apart between each other due to the action of the springs.

When the needle goes down, the small arms jointly go down, and due to the action of the springs, they remain spaced-apart between each other in a manner that the lower small arm first touches the support of the aforementioned switch valve. The needle continues to go down and the overlying small arm reaches the lower small arm, and so on, until all arms are lying one on top of the other, a condition which corresponds to a complete insertion of the needle in the injector. In this way, the needle is kept straight during its downward movement by the superimposed arms, the holes of which remain perfectly aligned. While the small arms move down, the springs which stress the arms are compressed in such a manner that, when the needle goes up, they place the small arms once again in the starting position.

As already mentioned, the invention also relates to a switch valve for an automatic sampling apparatus, applicable to a non-vaporizing on-column injector for liquid samples in a gas chromatographic capillary column, of the type comprising a main vertical duct for the passage of the injection syringe needle, closed at least at its lower end by sealing septum, characterized in that it comprises at least two secondary ducts, the first coming out at an intermediate point of the main duct and the second at its bottom part, the latter secondary duct being connected to a source of gas under pressure, while the first being connected to an exhaust.

The invention will now be described with reference to the attached drawings.

BRIEF DESCRIPTION OF THE DRAWINGS

FIG. 3 is a partial, cross-sectional side view of the device driving the sample injection needle, showing the needle partially inserted into the switch valve; and FIG. 4 is a partial, cross-sectional side view of the device driving the sample injection needle similar to that shown in FIG. 3, but with the needle being totally introduced into the injector.

DESCRIPTION OF THE PREFERRED EMBODIMENT

Figure 1:
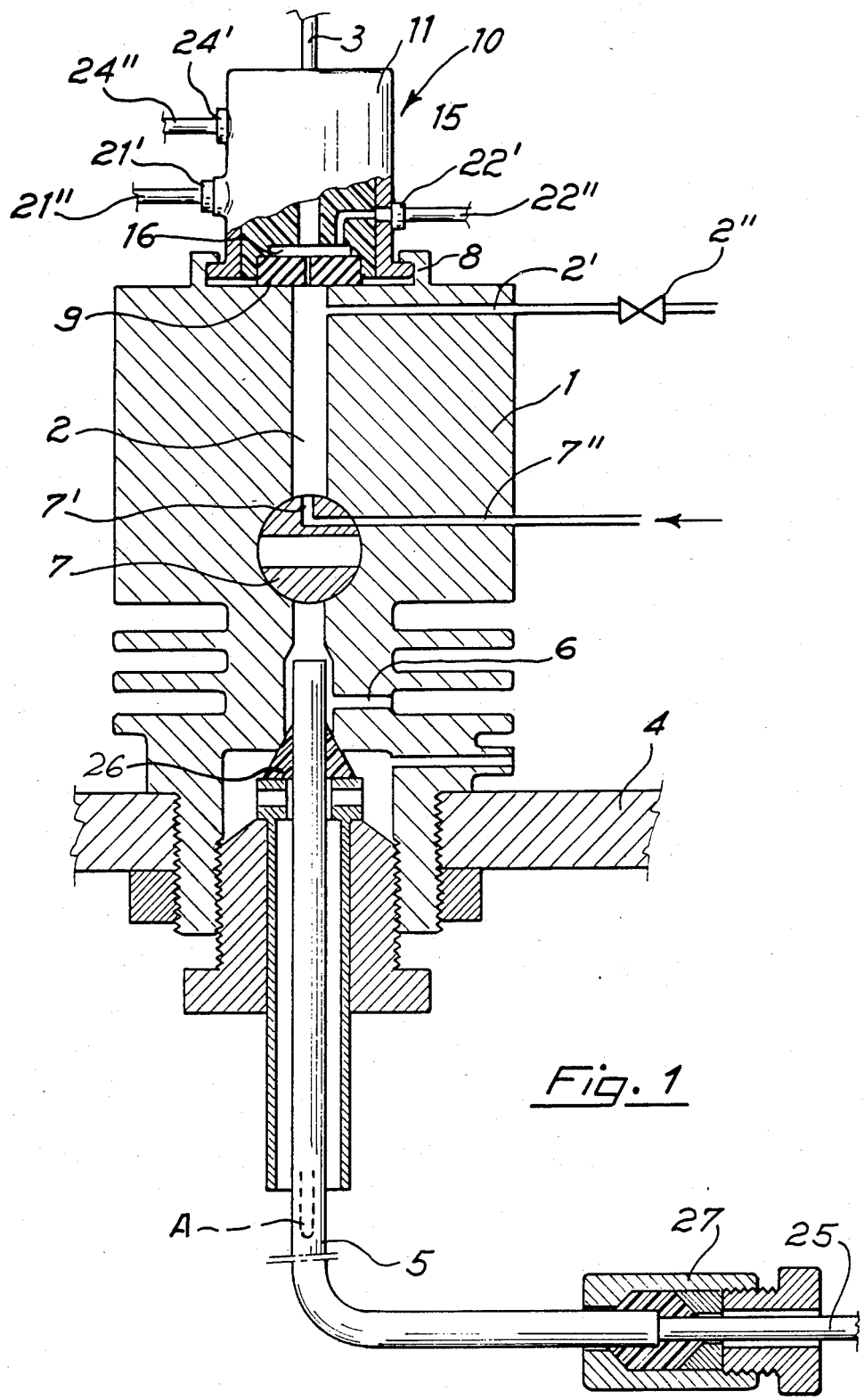
FIG. 1 is a longitudinal, partial cross-sectional view of a switch valve mounted onto an on-column type injector in an automatic sampling machine.

Referring to the aforementioned figures, reference numeral 1 indicates the body of an on-column type injector, for example, such as the one described and illustrated in U.S. Pat. No. 4,269,608.

The injector body 1 includes a duct 2 for the passage of a needle 3 of a syringe for the injection of a sample to be analyzed, connected to an automatic sampler, and fixed to the upper wall 4 of an oven housing a gas chromatographic pre-column 5. A duct 6 allows for the introduction of carrier gas into the duct 2, downstream of a valve 7 adapted for closing the duct. The duct 2 can be washed in the period between subsequent injections by an inert gas, for example, nitrogen. For this purpose, the valve 7 can optionally include an L-shaped secondary duct 7' which, when the valve is closed as illustrated in FIG. 1, connects to a duct 7" sending gas to the duct 2. With the valve 7 closed, the secondary duct 7' and duct 7" are arranged in fluid communication with an upper exhaust opening 2' provided in the body 1, which opening is controlled by a valve 2". The duct 2' and valve 2" can be eliminated, if desired, however, for good injector operation, their inclusion is preferred especially where particular conditions exist.

Figure 2:
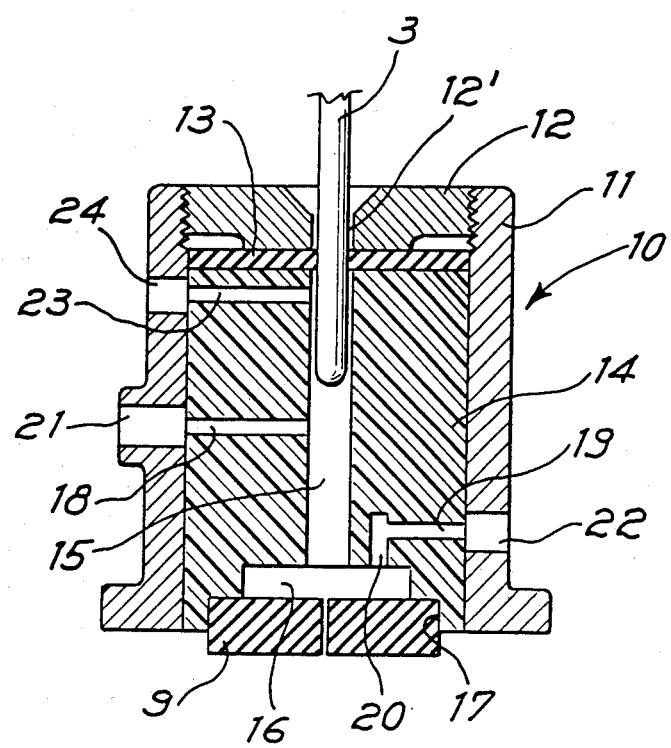
FIG. 2 is a detailed cross-sectional view of the switch valve shown in FIG. 1.

A switch valve 10 is mounted onto the injector body 1 adjacent to the inlet section of the duct 2 by means of a bayonet joint 8 and a sealing septum or seal gasket 9. As shown in FIG. 2, the valve 10 is constructed of a cylindrical body 11 made of metal having an axial bore, the upper end of which is closed by means of a screw cap 12 provided with an axial hole 12'. Inside the body 11, starting from its top, there are provided a rubber septum 13, an element 14 made of stiff chemically inert plastic material, for example, TEFLON which is a synthetic fluorine containing resin, and the seal gasket 9. The seal gasket 9 has the shape of a so-called "pierced septum". The cap 12 presses the seal gasket 9 against the injector body 1 and allows the seal gasket to carry out a sealing action between the valve 10 and the injector duct 2. The element 14 has an axial through hole 15, which adjacent to its bottom end, becomes larger to form a small chamber 16 and a seat 17 for partly housing the seal gasket 9. The thickness of the rubber septum 13 is relatively thin, while the seal gasket 9 is pre-pierced coaxially with the hole 15, in order to permit easy passage of the needle 3 of the injection syringe.

The element 14, besides the axial hole 15, also includes two radial holes 18 and 19, respectively, communicating with the duct 15 and with the chamber 16 via axial hole 20. Additional holes 21 and 22, provided in the cylindrical envelope of body 11, are respectively aligned with the radial holes 18 and 19 of the element 14. As shown in FIG. 1, this construction permits the fluid connection of duct 15, by means of fittings 21' and 22', to a collecting tank or an exhaust for the washing liquid or the excess sample via a duct 21' and to a gas source via a duct 22".

The end of the gas chromatographic pre-column 5 is inserted into the bottom end of the injector duct 2. The pre-column 5 is fixed in sealed engagement to the injector body 1 by means of a gasket 26, and is connected at its opposite end to the gas chromatographic column 25 by means of a joint 27, which can be of any known type.

In order to allow the use of syringe needles having sufficient strength to pass through the seal gasket 9 without being deformed, the internal diameter of the pre-column 5 is greater than or equal to 0.5 mm. As a consequence, the injector duct 2 also has a diameter greater than or equal to 0.5 mm, as well as the axial through hole 15 for the syringe needle in the switch valve 10.

The operation of the switch valve 10 will be described with reference to the following description of the injection steps for a sample to be analyzed and subsequent washing steps of the automatic sampler. During operation of the automatic sampler, the needle 3 of the injection syringe is inserted into the switch valve 10 and moved between a top position, shown in FIG. 2, in which the needle tip finds itself between the septum 13 and the radial hole 18, and a bottom position indicated by the reference A in FIG. 1, in which the needle tip finds itself inside the pre-column 5.

The steps of washing and elimination of the excess injected sample, prior to performing a subsequent sample analysis, occurs when the needle 3 corresponds to the needle top position. On the other hand, the step of sample introduction into the pre-column 5, occurs when the needle 3 corresponds to the needle bottom position. At the end of each sample injection, the needle 3 is moved to the top position and fed with washing liquid and subsequently with the sample to be analyzed, which is drawn from a vial and sent to the syringe. Simultaneously through the hole 19, the duct 15 receives a gas flow, the pressure of which is controlled in a way so as to create a gaseous cap in the bottom portion of the duct 15 under the needle 3.

More specifically, during the step, the pressure of the gas entering from hole 19 is such so as to prevent the sample within the needle 3 from flowing down through the duct 15, and from there, through the hole in the seal gasket 9 and into the injector body 1. This is achieved by controlling the gas flow rate and pressure so that the sample can flow out of the needle 3 and then through the hole 18, but cannot flow down through the duct 15 and into the hole of seal gasket 9. When the injection syringe and the needle 3 are filled with the sample and the needle is in the needle top position, the device actuating movement of the needle stops, for a time period which can be regulated, sufficient for the gas entering the radial hole 19 to eliminate any sample trace from both the duct 15 and the external walls of the needle.

During the subsequent needle movement towards the needle bottom position, the gas current is effective to dry the outer walls of the needle 3 to avoid any injector pollution. In order to improve the above gas action, the element 14 immediately below its top end, can include a radial hole 23 coaxially arranged with a hole 24 provided in the cylindrical envelope 11 of the switch valve 10. This construction allows the gas to travel up along the outer walls of the needle 3 and to dry them up as far as the rubber septum 13, then flowing out through the fitting 24' and duct 24''. The duct 24'' can be controlled by a suitable exhaust valve (not shown). When this time period is over, the device controlling the movement of the needle 3 actuates again, the needle now reaching its bottom position for sample injection into the gas chromatographic capillary column. It should be noted that, due to the drying action performed by the gas introduced through the hole 19, sample traces are prevented from being dragged by the needle 3 through the seal gasket 9 and into the injector body 1.

At the end of the injection step and when the needle 3 is again in the needle top position, the washing cycle of the entire path of the injected sample begins, starting from the sample drawing end to the needle tip. In order to prevent sample residue present in the syringe and in the needle 3, as well as the washing fluid itself, from going beyond the rubber seal gasket 9 and penetrating the duct 2 of the injection body 1, gas is fed through the hole 19. In this way, as in during the step of sample metering, the washing liquid is pushed by the gas action into the hole 18 from which, through a suitable duct connected to the hole 21, it flows into a container or an exhaust opening.

When all traces of the previously injected sample have been eliminated from the needle 3 and syringe, feeding of the injection syringe with washing liquid is reduced, while gas feeding to the hole 19 still continues. In this way, the needle 3 is dried by the gas which eliminates any remaining traces of washing liquid. The automatic sampler is thus made available for providing a new sample to the injection syringe, the switch valve 10 and the duct 2 of the injector body 1 now being perfectly clean. During this step, it is possible to wash the lower valve 7 as shown in FIG. 1, through the ducts 7'', 7' and 2'. It is to be understood that in the event the valve 7 which is automatically controlled, is operable for carrying out washing of duct 2 when the needle 3 is removed, as described above, the valve can have a configuration of the type described in U.S. Pat. No. 4,403,520.

FIGS. 3 and 4 show a device adapted for driving the needle 3 for sample injection. The device is constructed of a support 30 holding in its lower part the needle 3 and in its upper part a duct 31 from which the sample to be analyzed is introduced. The support 30 is integral to a vertical tube 32, the bottom end of which receives in a telescopic manner, a tube 33 to which a small arm 33' is fixed. In the bottom end of the tube 33, there is inserted a small cylinder 34 provided on its end with a small arm 35.

The tube 32 which drives the support 30, is secured at its lower end by means of a small arm 36, to a hydraulic or pneumatic piston 37 for controlling the up and down movement of the needle 3. The injection needle 3 is inserted into a suitable hole 36' provided in the small arm 36 and secured therein by a screw 38.

The tube 33 and the small cylinder 34 are kept spaced-apart in telescopic engagement by the action of springs 39 and 40 placed inside them, and are driven in their movement by a vertical rod 41. The vertical rod 41 is coaxially arranged within the tubes 32 and 33, and is connected at its lower end to the small cylinder 34. A lock 43 provided at the top of the vertical rod 41 is capable of maintaining, against the action of springs 39 and 40, the small cylinder 34 and the tubes 32 and 33 in their position of reciprocal telescopic engagement.

The small arms 33' and 35 are each provided with a pierced rubber septum 42, in which the injection needle 3 is slidingly inserted. The holes of the septum 42 are precision aligned with each other and with the hole 36' of the small arm 36. In this way, the needle 3 is kept straight during its movement by the superimposed and spaced-apart small arms 33', 35 and 36, the movements of which occur along a path which is parallel to the preferred path of travel of the needle 3.

In particular, when the needle 3 goes down, the small arms 33', 35 and 36 go down jointly, and due to the action of the springs 39 and 40, remain spaced-apart until the lower small arm 35 first reaches the support of the switch valve 10. The needle 3 continues its downward run and the small intermediate arm 33' reaches the lower small arm 35. Simultaneously, the small cylinder 34 enters the tube 33 and the spring 40 is compressed. Finally, the small arm 36 reaches the small arm 33', while the tube 33 enters the tube 32 and the spring 39 is compressed. This condition corresponds to the complete insertion of the needle 3 into the injector body 1. When the piston 37 actuates the upward movement of the needle 3, the action of the springs 39 and 40 restores the initial equally spaced position of the small arms 33', 35 and 36.

We claim:

1. An automatic sampling apparatus for the injection of samples to be analyzed in a gas chromatographic capillary column, said sampling apparatus having operably associated therewith an automatic device for feeding individual samples to be analyzed and a washing fluid to an injection syringe to be inserted into said capillary column, said sampling apparatus comprising an injection sryinge operatively associated with said automatic device, a housing containing said capillary column, an injector of the non-vaporizing direct on-column type secured to said housing, said injector having a first axial bore extending therethrough in fluid communication with said capillary column, a switch valve sealingly secured to said injector and having a second axial bore extending therethrough for receiving a portion of said injection syringe and arranged in coaxial alignment with said first axial bore of said injector, actuating means for reciprocally advancing and withdrawing said injection syringe between said first and second axial bores of said injector and said switch valve, said actuating means including a first arm adapted for reciprocal movement along a linear path for advancing and withdrawing said injection syringe and having said injection syringe secured thereto, a second arm spaced from said first arm and having an opening slidingly receiving said injection syringe, and a third arm spaced from said second arm, and having an opening slidingly receiving said injection syringe, said openings of said second and third arms being arranged along said linear path, whereby said injection syringe is guided along said linear path by said openings in said second and third arms, a first sealing septum separating said first and second axial bores, a second sealing septum provided within said second axial bore and spaced from said first sealing septum to define a first chamber therebetween, a second chamber having a diameter greater than that of said first chamber arranged within said switch valve adjacent said first sealing septum and in fluid communication with said first chamber, and first, second and third ducts provided within said switch valve, said first duct arranged intermediate of said first and second sealing septums in fluid communication between said first chamber and an external exhaust, said second duct arranged adjacent said second chamber in fluid communication therewith and a source of a gas under pressure, and said third duct arranged adjacent said second sealing septum in fluid communication between said first chamber and an external exhaust.

2. The sampling apparatus of claim 1, wherein the diameter of said first and second axial bores of said injector and said switch valve are at least 0.5 mm.

3. The sampling apparatus of claim 2 further including a gas chromatographic pre-column arranged within said housing in fluid communication between said capillary column and one end of said first axial bore of said injector, and wherein the diameter of said pre-column is at least 0.5 mm.

4. The sampling apparatus of claim 1 wherein said actuating means further includes a telescopic assembly attached to said first, second and third arms, said telescopic assembly comprising a first hollow member attached to said first arm, a second hollow member attached to said second arm and telescopically received within said first hollow member, a third member attached to said third arm and telescopically received within said second hollow member, and biasing means arranged within a hollow of said first and second hollow members for maintaining said first, second and third arms in spaced-apart superimposed relationship while permitting their arrangement in superimposed contiguous relationship upon compression of said biasing means.

5. The sampling apparatus of claim 4 wherein said biasing means comprises a first spring contained within a hollow of said first hollow member, a second spring contained within a hollow of said second hollow member, a rod extending longitudinally within said first and second hollow members, said rod having one end secured to said third member and another end slidingly received through a top portion of said first hollow member, and locking means attached to said another end of said rod to maintain said first hollow member, said second hollow member and said third member in telescopic engagement when said first and second springs maintain said first, second and third arms in said spaced-apart superimposed relationship.

6. The sampling apparatus of claim 1 wherein said source of a gas under pressure is supplied to said first chamber through said second duct at a pressure sufficient to prevent said sample or said washing fluid from contacting said first sealing septum.

7. The sampling apparatus of claim 1 wherein said first sealing septum has an opening extending therethrough providing communication between said first and second axial bores.

8. An automatic sampling apparatus for the injection of samples to be analyzed in a gas chromatographic capillary column, said sampling apparatus having operably associated therewith an automatic device for feeding individual samples to be analyzed and a washing fluid to an injection syringe to be inserted into said capillary column, said sampling apparatus comprising an injection syringe operatively associated with said automatic device, a housing containing said capillary column, an injector of the non-vaporizing direct on-column type secured to said housing, said injector having a first axial bore extending therethrough in fluid communication with said capillary column, a switch valve secured to said injector and having a second axial bore extending therethrough for receiving a portion of said injection syringe and arranged in coaxial alignment with said first axial bore of said injector, said switch valve adapted for preventing said sample and said washing fluid supplied to said injection syringe from communicating with said first axial bore of said injector, said switch valve comprising a first sealing septum separating said first and second axial bores, and first and second ducts, said first duct arranged intermediate of said second axial bore in fluid communication between said second axial bore and an external exhaust, said second duct arranged adjacent said first sealing septum in fluid communication between said second axial bore and a source of a gas under pressure.

9. The sampling apparatus of claim 8 wherein said switch valve further includes a second sealing septum provided within said second axial bore and spaced from said first sealing septum to define a first chamber therebetween, a second chamber having a diameter greater than that of said first chamber arranged within said switch valve adjacent said first sealing septum and providing fluid communication between said second duct and said first chamber, and a third duct arranged adjacent said second sealing septum in fluid communication between said first chamber and an external exhaust.

10. The sampling apparatus of claim 9 wherein said source of a gas under pressure is supplied to said first chamber through said second duct at a pressure sufficient to prevent said sample or said washing fluid from contacting said first sealing septum.

11. The sampling apparatus of claim 8 further including actuating means for reciprocally advancing and withdrawing said injection syringe between said first and second axial bores of said injector and said switch valve, said actuating means including a first arm adapted for reciprocal movement along a linear path for advancing and withdrawing said injection syringe and having said injection syringe secured thereto, a second arm spaced from said first arm and having an opening slidingly receiving said injection syringe, and a third arm spaced from said second arm and having an opening slidingly receiving said injection syringe, said openings of said second and third arms being arranged along said linear path, whereby said injection syringe is guided along said linear path by said openings in said second and third arms.

12. The sampling apparatus of claim 11 wherein said actuating means further includes a telescopic assembly attached to said first, second and third arms, said telescopic assembly comprising a first hollow member attached to said first arm, a second hollow member attached to said second arm and telescopically received within said first hollow member, a third member attached to said third arm and telescopically received within said second hollow member, and biasing means arranged within a hollow of said first and second hollow members for maintaining said first, second and third arms in spaced-apart superimposed relationship while permitting the arrangement in superimposed contiguous relationship upon compression of said biasing means.

13. The sampling apparatus of claim 12 wherein said biasing means comprises a first spring contained within a hollow of said first hollow member, a second spring contained within a hollow of said second hollow member, a rod extending longitudinally within said first and second hollow members, said rod having one end secured to said third member and another end slidingly received through a top portion of said first hollow member, and locking means attached to said another end of said rod to maintain said first hollow member, said second hollow member and said third member in telescopic engagement when said first and second springs maintain said first, second and third arms in said spaced-apart superimposed relationship.

14. An automatic sampling apparatus for the injection of samples to be analyzed in a gas chromatographic capillary column, said sampling apparatus having operably associated therewith an automatic device for feeding individual samples to be analyzed and a washing fluid to an injection syringe to be inserted into said capillary column, said sampling apparatus comprising an injection syringe operatively associated with said automatic device, a housing containing said capillary column, an injector of the non-vaporizing direct on-column type secured to said housing, said injector having a first axial bore extending therethrough in fluid communication with said capillary column, a switch valve secured to said injector, said switch valve comprising an elongated hollow shell, an elongated body within said shell having a second axial bore extending therethrough for receiving a portion of said injection syringe and arranged in coaxial alignment with said first axial bore of said injector, a first sealing septum arranged within said hollow shell at one end thereof between said elongated body and said housing, securing means for securing said hollow shell to said housing, whereby said first sealing septum is compressed to provide a fluid seal between said elongated body and said housing, a second sealing septum arranged within said hollow shell at another end thereof, a cap having an opening in coaxial alignment with said second bore received within said another end of said hollow shell, whereby said second sealing septum is compressed between said cap and said elongated body to provide a fluid seal thereat, actuating means for reciprocally advancing and withdrawing said injection syringe between said first and second axial bores of said injector and said switch valve, said actuating means including a first arm adapted for reciprocal movement along a linear path for advancing and withdrawing said injection syringe and having said injection syringe secured thereto, a second arm spaced from said first arm and having an opening slidingly receiving said injection syringe, and a third arm spaced from said second arm and having an opening slidingly receiving said injection syringe, said openings of said second and third arms being arranged along said linear path, whereby said injection syringe is guided along said linear path by said openings in said second and third arms, said actuating means including a telescopic assembly attached to said first, second and third arms, said telescopic assembly comprising a first hollow member attached to said first arm, a second hollow member attached to said second arm and telescopically received within said first hollow member, a third member attached to said third arm and telescopically received within said second hollow member, and biasing means arranged within a hollow of said first and second hollow members for maintaining said first, second and third arms in spaced-apart superimposed relationship while permitting the arrangement in superimposed contiguous relationship upon compression of said biasing means.

15. The sampling apparatus of claim 14 wherein said biasing means comprises a first spring contained within a hollow of said first hollow member, a second spring contained within a hollow of said second hollow member, a rod extending longitudinally within said first and second hollow members, said rod having one end secured to said third member and another end slidingly received through a top portion of said first hollow member, and locking means attached to said another end of said rod to maintain said first hollow member, said second hollow member and said third member in telescopic engagement when said first and second springs maintain said first, second and third arms in said spaced-apart superimposed relationship.

16. The sampling apparatus of claim 14 further including a first duct extending through said hollow shell and said elongated body, and a second duct extending through said hollow shell and said elongated body, said first duct arranged intermediate of said elongated body in fluid communication between said second axial bore and an external exhaust, said second duct arranged adjacent said first sealing septum in fluid communication between said second axial bore and a source of gas under pressure.

17. The sampling apparatus of claim 16 further including a third duct arranged adjacent said second sealing septum in fluid communication between said second axial bore and an external exhaust.

18. The sampling apparatus of claim 16 wherein said source of a gas under pressure is supplied to said second axial bore through said second duct at a pressure sufficient to prevent said sample or said washing fluid from contacting said first sealing septum.

19. A method for feeding liquid samples to be analyzed to a capillary column of a gas chromatograph by means of an automatic sampling apparatus, said sampling apparatus having operably associated therewith an automatic device for feeding individual samples to be analyzed and a washing fluid to an injection syringe to be inserted into said capillary column, said automatic sampling apparatus including an injector of the non-vaporizing direct on-column type having a first axial bore extending therethrough in fluid communication with said capillary column, and a switch valve secured to said injector and having a second axial bore extending therethrough for receiving a portion of said injection syringe and arranged in coaxial alignment with said first axial bore of said injector, said switch valve adapted for preventing said sample and said washing fluid supplied to said injection syringe from communicating with said first axial bore of said injector, and actuating means for reciprocally advancing and withdrawing said injection syringe between said first and second axial bores of said injector and said switch valve, said method comprising the steps of washing said injection syringe and said second axial bore with a washing fluid supplied thereto from said automatic device while maintaining said injection syringe withdrawn into said second axial bore of said switch valve, feeding a fluid sample to be analyzed through said injection syringe and into said second axial bore by means of said automatic device while maintaining said injection syringe withdrawn into said second axial bore of said switch valve, introducing a gas under a sufficient pressure into said second axial bore to prevent said fluid sample and said washing fluid within said second axial bore from entering said first axial bore of said injector, advancing said injection syringe from within said second axial bore into said first axial bore of said injector by means of said actuating means, and injecting said fluid sample to be analyzed into said capillary column by means of said automatic device.

20. The method of claim 19 further including the step of removing said fluid sample and said washing fluid within said second axial bore through a duct provided within said switch valve in fluid communication between said second axial bore and an external exhaust.

21. An automatic sampling apparatus for the injection of samples to be analyzed in a gas chromatographic capillary column, said sampling apparatus having operably associated therewith an automatic device for feeding individual samples to be analyzed and a washing fluid to an injection syringe to be inserted into said capillary column, said sampling apparatus comprising an injection syringe operatively associated with said automatic device, a housing containing said capillary column, an injector of the non-vaporizing direct on-column type secured to said housing, said injector having a first axial bore extending therethrough in fluid communication with said capillary column, a switch valve sealingly secured to said injector and having a second axial bore extending therethrough for receiving a portion of said injection syringe and arranged in coaxial alignment with said first axial bore of said injector, actuating means for reciprocally advancing and withdrawing said injection syringe between said first and second axial bores of said injector and said switch valve, said actuating means including a first arm adapted for reciprocal movement along a linear path for advancing and withdrawing said injection syringe and having said injection syringe secured thereto, a second arm spaced from said arm and having an opening slidingly receiving said injection syringe, and a third arm spaced from said second arm, and having an opening slidingly receiving said injection syringe, said openings of said second and third arms being arranged along said linear path, whereby said injection syringe is guided along said linear path by said openings in said second and third arms, said actuating means including a telescopic assembly attached to said first, second and third arms, said telescopic assembly comprising a first hollow member attached to said first arm, a second hollow member attached to said second arm and telescopically received within said first hollow member, a third member attached to said third arm and telescopically received within said second hollow member, and biasing means arranged within a hollow of said first and second hollow members for maintaining said first, second and third arms in spaced-apart superimposed relationship while permitting their arrangement in superimposed contiguous relationship upon compression of said biasing means.

22. An automatic sampling apparatus for the injection of samples to be analyzed in a gas chromatographic capillary column, said sampling apparatus having operably associated therewith an automatic device for feeding individual samples to be analyzed and a washing fluid to an injection syringe to be inserted into said capillary column, said sampling apparatus comprising an injection syringe operatively associated with said automatic device, a housing containing said capillary column, an injector of the non-vaporizing direct on-column type secured to said housing, said injector having a first axial bore extending therethrough in fluid communication with said capillary column, a switch valve secured to said injector, said switch valve comprising an elongated hollow shell, an elongated body within said shell having a second axial bore extending therethrough for receiving a portion of said injection syringe and arranged in coaxial alignment with said first axial bore of said injector, a first sealing septum arranged within said hollow shell at one end thereof between said elongated body and said housing, securing means for securing said hollow shell to said housing, whereby said first sealing septum is compressed to provide a fluid seal between said elongated body and said housing, a second sealing septum arranged within said hollow shell at another end thereof, a cap having an opening in coaxial alignment with said second bore received within said another end of said hollow shell, whereby said second sealing septum is compressed between said cap and said elongated body to provide a fluid seal thereat, a first duct extending through said hollow shell and said elongated body, and a second duct extending through said hollow shell and said elongated body, said first duct arranged intermediate of said elongated body in fluid communication between said second axial bore and an external exhaust, said second duct arranged adjacent said first sealing septum in fluid communication between said second axial bore and a source of gas under pressure, wherein said source of a gas under pressure is supplied to said second axial bore through said second duct at a pressure sufficient to prevent said sample or said washing fluid from contacting said first sealing septum.

23. The sampling apparatus of claim 22 further including a third duct arranged adjacent said second sealing septum in fluid communication between said second axial bore and an external exhaust.

* * * * *